(12) United States Patent
Leung

(10) Patent No.: US 6,489,356 B2
(45) Date of Patent: *Dec. 3, 2002

(54) METHOD FOR TREATING PAIN IN HUMANS

(76) Inventor: Edward Leung, 116 Rose Sky Ct., Cary, NC (US) 27513

( * ) Notice: Subject to any disclaimer, the term of this patent is extended or adjusted under 35 U.S.C. 154(b) by 57 days.

This patent is subject to a terminal disclaimer.

(21) Appl. No.: 09/883,474

(22) Filed: Jun. 18, 2001

(65) Prior Publication Data

US 2002/0055535 A1 May 9, 2002

Related U.S. Application Data

(63) Continuation-in-part of application No. 09/654,994, filed on Sep. 5, 2000, now Pat. No. 6,248,774.

(51) Int. Cl.$^7$ ............................................. A61K 31/38

(52) U.S. Cl. ..................................................... 514/443

(58) Field of Search ........................................ 514/443

(56) References Cited

U.S. PATENT DOCUMENTS

| 5,691,317 | A |   | 11/1997 | Sollevi |         |
|-----------|---|---|---------|---------|---------|
| 5,939,432 | A | * | 8/1999  | Baraldi | 514/301 |
| 6,004,945 | A |   | 12/1999 | Fukunaga |        |
| 6,177,444 | B1 |  | 1/2001  | Baraldi |         |
| 6,180,616 | B1 |  | 1/2001  | Fukunaga |        |
| 6,194,449 | B1 |  | 2/2001  | Baraldi |         |
| 6,248,774 | B1 | * | 6/2001  | Leung   | 514/443 |
| 6,323,214 | B1 |  | 11/2001 | Baraldi |         |

OTHER PUBLICATIONS

Sollevi, A. Adenosine for pain control. Acta Anaesthesiol. Scand. Suppl. 110: 135–136, 1997.

Belfrage M., Segerdahl M., Arner S., Sollevi A. The safety and efficacy of intrathecal adenosine in patients with chronic neuropathic pain. Anesth. Analg. 89: 136–142, 1999.

Ralevic V. and Burnstock, G. Receptors for Purines and Pyrimidines. Pharmacol. Rev. 50: 413–492, 1998.

Bruns, R.F., Fergus, J.H., Coughenour, L.L., Courtland, G.g., Pugsley, T.A., Dodd., J. H., Tinney, F.J. Structure–activity relationships for enhancement of adenosine A1 receptor binding by 2–amino–3–benzoylthiophenes. Mol. Pharm. 38: 950–958, 1990.

van der Klein, P.A., Kourounakis, A.P. and Ijzerman, A.P. Allosteric modulation of the adenosine A(1) receptor. Synthesis and biological evaluation of novel. 2–amino–3–benzoylthiophenes as allosteric enhancers of agonist binding. J Med Chem 42: 3629–3625, 1999.

Bruns, R.F. and Fergus, J.H. Allosteric enhancement of adenosine A1 receptor binding and function by 2–amino–3–benzoylthiophenes. Mol. Pharmacol. 38: 939–949, 1990.

Poulson, S.A. and Quinn, R.J. Adenosine receptors: new opportunities for future drugs. Bioorg. Med. Chem. 6:619–641, 1998.

Linden, J. Allosteric enhancement of adenosine receptors. In Purinegic Approaches in Experimental Therapeutics, edited by K.A. Jacobson and M.F. Jarvis, 1997 Wiley–Liss, pp85–97.

Leung, E. Walsh, L.K.M., Flippin, L.A. Kim, E.J., Lazar, DE.A., Seran, C.S., Wong, E.H.F. and Eglen, R.M. Enhancement of adenosine A1 receptor functions by benzoylthiophenes in guinea pig tissues in vitro. Naunyn–Schmiedeberg's Arch. Pharmacol. 352: 206–212, 1995.

Shryoick, J.D., Ozeck, M.J. and Belardinelli, L. Inverse agonists and neutral antagonists of recombinant human A1 adenosine receptors stably expressed in chinese hamster ovary cells. Mol. Pharmacol. 53: 886–893, 1993.

Kim, S.H. and Chung, J.M. An experimental model for periphereal neuropathy produced by segmental spinal nerve ligation in the rat. Pain, 50: 355–363, 1992.

Sawynok, J. Purines and Nociception. In Purinergic Approaches in Experimental Therapeutics, Edited by K.A. Jacobson and M.F. Jarvis. 1997 Wiley–Liss, pp495–513.

Yaksh, T.L. Spinal systems and pain processing: development of novel analgesic drugs with mecahnistically defined models. Trends in Pharmacological Sciences 20, 329 337, 1999.

Jarvis, M.F., Yu, H., Kohlhass, K., Alexander, K, Lee, C.–H., Jiang, M., Bhagwat, S.S., Williams, M. and Kowaluk, E.A. ABT–702.

(4–Amino–5–(3–bromophenyl)–7–(6–morpholino–pyridin–3–yl)pyrido[2,3–d]pyrimidine), a novel orally effective adenosine kinase inhibitor with analgesic and anti–inflammatory properties: I.

(List continued on next page.)

Primary Examiner—Raymond Henley, III

(57) ABSTRACT

The present invention relates to Compound T62, pharmaceutically acceptable salts thereof, and their use in medicine as allosteric adenosine $A_1$ receptor enhancers and uses including treatment of pain, for example, persistent chemical pain, neuropathic pain and acute pain states such as that induced by chemical irritation, gastrointestinal disturbance, migraine and all forms of headache. Compound T62 is represented by the formula:

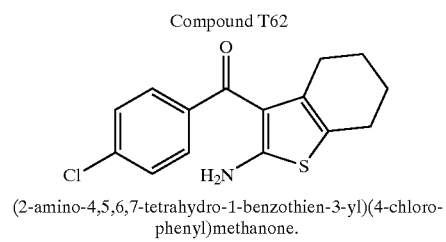

(2-amino-4,5,6,7-tetrahydro-1-benzothien-3-yl)(4-chlorophenyl)methanone.

26 Claims, 6 Drawing Sheets

OTHER PUBLICATIONS

In vitro characterization and acute antinociceptive effects in the mouse. J. Pharm. Exp. Ther. 295, 1156–1164, 2000.

Kowaluk, E.A., Mikusa, J., Wismer, C.T., Zhu, C.Z., Schweitzer, E., Lynch, J.L., Lee, C.-H., Jiang, M, Bhagwat, S.S., Gomtsyan, A., McKie, J., Cox, B.F., Polakowski, J. J., Reinhart, G., Williams, M. and Jarvis, M.F. ABT–702 (4–amino–5–(3–bromophenyl)–7–(6–morpholino–pyridin–3–yl)pyrido[2,3–d]pyrimidine), a novel orally effective adensoine kinase inhibitor with analgesic and anti–inflammatory properties.J. Pharm. Ther. 295, 1165–1174, 2000.

McGaraughty, S., Chu, K.L., Wismer, C.T., Mikusa, J., Zhu, C.Z., Cowart, M., Kowaluk, E.a. and Jarvis, M.F. Effects of A–134974, a novel adenosine kinase inhibitor, on carrageenan–induced inflammatory hyperalgesia and locomotor activity in rats: evaluation of the sites of action. J. Pharm Exp Ther 296 501–509 2001.

* cited by examiner

METHOD FOR TREATING PAIN IN HUMANS

CROSS REFERENCES TO RELATED APPLICATIONS

This is a continuation-in-part to U.S. patent application Ser. No. 09/654,994 filed Sep. 5, 2000 now U.S. Pat. No. 6,248,774, by Edward Leung and titled "Method for Treating Hyper-Excited Sensory Nerve Functions in Humans."

BACKGROUND OF THE INVENTION

The present invention relates to methods and compositions for treating various forms of pain in mammals. Although the present invention is expected to be useful for virtually all pain types, it is most potent for pain involving hypersensitivity of the nociceptive pathway such as inflammatory pain, persistent chemical pain, and neuropathic pain. At higher doses, the present invention is also effective in acute pain states such as that induced by chemical irritation, gastrointestinal disturbance, migraine and all forms of headache.

Inflammatory pain can occur when tissue is damaged, as can result from surgery or due to an adverse physical, chemical or thermal event or to infection by a biologic agent. Although inflammatory pain is generally reversible and subsides when the injured tissue has been repaired or the pain inducing stimulus removed, present methods for treating inflammatory pain have many drawbacks and deficiencies. Thus, the typical oral, parenteral or topical administration of an analgesic drug to treat the symptoms of pain or of, for example, an antibiotic to treat inflammatory pain causation factors can result in widespread systemic distribution of the drug and undesirable side effects. Additionally, current therapy for inflammatory pain suffers from short drug efficacy durations which necessitate frequent drug re-administration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule.

Chemically induced pain may occur when a patient is exposed to chemical agents that trigger pain response. Commonly, chemical pain is used to test anesthetic or analgesic efficacy of treatment methods.

Some examples of neuropathic pain are diabetic neuropathy, post-herpetic neuralgia (shingles), trigeminal neuralgia, pain associated with AIDS infection and treatment, whip-lash pain, pain due to cancer treatment, phantom limb pain, traumatic injury, complex regional pain syndrome and pain due to peripheral vascular disease.

The development of hyper-excited sensory nerve function has been described by Sollevi 1997 (1). These symptoms are often manifested as neuropathic pain. Neuropathic pain is a persistent, chronic pain usually described as a burning, shooting or lancinating sensation without an obvious cause. These symptoms are often associated with damage to nerves or nerve fibers. Such pain is associated with the transmission of abnormal pain signals from injured peripheral nerves to neurons in the brain and spinal cord. Briefly, the sensory nervous system projects signals to the central nervous system (CNS), mediating information from the periphery to the brain. These comprise signals from sensors in peripheral tissues and other organs, sensitive for qualities like touch, temperature changes, vibration, painful stimuli, pressure, vision, hearing, smell, taste and balance. This sensory nervous system is an important physiological control in the subject's relation to the environment.

The sensory nervous system can be damaged by various types of trauma, such as infections and mechanical lesions including whip-lash injury, diseases such as diabetes and HIV infection, cancer or HIV treatments. This can result in disturbance in the signal transmission into the CNS, leading to reduced perception of sensory signals (hypoestesia) as well as hyper-function (more excited signals in the CNS) due to some largely unknown changes in the nerve transmission process (neuropathic damage). The neuropathic condition with hyper-excitation is described as a "wind-up" phenomenon and often involves several of the above mentioned sensory functions.

This may therefore be associated with decreased thresholds for touch and temperature (hyperesthesia), discomfort in the perception for touch and temperature (dysesthesia), discomfort or pain with touch, pressure and/or temperature stimulation (allodynia), and hypersensitivity to pain stimuli (hyperalgesia), balance disturbance, disturbance of auditory type (tinnitus) as well as ganglionic dysfunction. These types of hyper-reactive sensory nerves may develop after various types of trauma, and are called chronic when persistent for more than 3–6 months.

Adenosine, administered intravenously or intrathecally, has been proposed as a treatment for this sensory nerve hyper-reactivity (1, 2, 3). The objective of the treatment is to restore a normal perception of pain, as well as other sensory functions, in patients suffering from pathological hyper-excitation due to nerve damage.

Similarly adenosine has been proposed as treatment for other pain states derived from nociception including acute pain, tissue injury pain and nerve injury pain (15). Adenosine modulates the pain response by stimulating $A_1$ adenosine receptors present in the dorsal root of the spinal cord and higher brain centers (spraspinal mechanisms) (14). $A_1$ agonists have been shown to be effective treatment for every pain type in animal pain models (see Table 2 of, Yaksh, 1999, reference 15). However, $A_1$ agonists also cause cardiovascular side effects and CNS side effects such as heart block, hypotension and sedation.

Adenosine is an endogenous nucleoside present in all cell types of the body. It is endogenously formed and released into the extracellular space under physiological and pathophysiological conditions characterized by an increased oxygen demand/supply ratio. This means that the formation of adenosine is accelerated in conditions with increased high energy phosphate degradation. The biological actions of adenosine are mediated through specific adenosine receptors located on the cell surface of various cell types, including nerves (4). The hyper-reactive nerves increase adenosine release due to an increase in metabolic activity.

$A_1$ receptors are widely distributed in most species and mediate diverse biological effects. The following examples are intended to show the diversity of the presence of $A_1$ receptors rather than a comprehensive listing of all such receptors. $A_1$ receptors are particularly ubiquitous within the central nervous system (CNS), with high levels being expressed in the cerebral cortex, hippocampus, cerebellum, thalamus, brain stem, and spinal cord. Immunohistochemical analysis using polyclonal antisera generated against rat and human $A_1$ adenosine receptors has identified different labeling densities of individual cells and their processes in selected regions of the brain. $A_1$ receptor mRNA is widely distributed in peripheral tissues such as the vas deferens, testis, white adipose tissue, stomach, spleen, pituitary, adrenal, heart, aorta, liver, eye, and bladder. Only very low levels of $A_1$ receptors are thought to be present in lung, kidney, and small intestine.

The present invention relates to a class of compounds known as allosteric modulators or allosteric enhancers. Prior to the present invention and its parent (U.S. patent application Ser. No. 09/654,994), allosteric enhancers have only been described for the $A_1$ adenosine receptor (5, 6, 7). No allosteric modulators had been proven effective in neuropathic pain models at any concentration. $A_1$ the currently known enhancers are derivatives of the 2-amino-3-benzoylthiophenes first described by Bruns et al. (5). These benzoylthiophenes are not agonists at the endogenous $A_1$ adenosine receptor (5, 6, 8). Structurally, all known agonists for the $A_1$ adenosine receptor are derivatives of adenosine. The presence of an unmodified ribose ring is essential for agonist activity at the $A_1$ adenosine receptor (9). Benzoylthiophenes are not agonists at the $A_1$ adenosine receptor. Importantly, these compounds are antagonists at the $A_1$ adenosine receptor (5, 6, 7, 8). At low concentrations, these benzoylthiophenes enhance the effect of agonists. At higher concentrations, these compounds act as antagonists. Therefore, the concentration range where these compounds can enhance the effects of agonists is limited (8).

Mechanistically, benzoylthiophenes appeared to enhance $A_1$ adenosine receptor function by stabilizing the high affinity state of the receptor-G-protein complex (8, 10). This property is manifested as an increase in high affinity binding in radioligand binding reactions where an agonist radioligand is used to label the $A_1$ adenosine receptor. An enhancer that increases agonist binding can do so by either accelerating the association of agonist and receptor, or by retarding the dissociation of the "receptor-ligand" complex. Kinetic studies have shown the benzoylthiophenes to retard the dissociation of the "receptor-ligand" complex. In contrast, an agonist, or an antagonist will both compete with the radioligand for the binding site and accelerate the dissociation of the "receptor-ligand" complex (8). Since the benzoylthiophenes only selectively retard the dissociation of the "receptor-ligand" complex when an agonist radioligand is used, the benzoylthiophenes must bind to a site different from the agonist recognition site. This putative site is termed the allosteric site, and presumably, compounds that bind to this site and enhance the agonist effect are termed "allosteric enhancers".

Another challenge is that that wide distribution of adenosine receptors offers both opportunities and drawbacks for therapeutic intervention. As an example, $A_1$ adenosine receptors are found in the CNS, in heart and adipose tissue. Thus, agonists are capable of reducing free fatty acid levels in the blood through their interaction with adenosine $A_1$ receptors on fat cells. This is a useful feature in non-insulin dependent diabetes mellitus. However, the concomitant bradycardia and drop in mean arterial pressure due to interference with cardiovascular adenosine receptors are to be considered as serious side effects.

In the U.S. patent application Ser. No. 09/654,994, Compound T62 is disclosed in the parent application as being a potent allosteric adenosine $A_1$ receptor antagonist. However, as disclosed, Compound T62 is used in relatively low dosages and as such is most effective in the treatment of neuropathic pain.

BRIEF SUMMARY OF THE INVENTION

An object of the present invention is to provide a therapeutically useful enhancer with improved potency as an enhancer, and preferably, without antagonist property. The present invention describes the discovery of a compound that meets these criteria.

The present invention relates to a composition and a method for the treatment of hyper-excited sensory nerve functions, e.g., neuropathia in human subjects. The treatment method comprises oral administration, topical administration, subcutaneous administration, intravenous administration, or intrathecal administration of an allosteric enhancer at the adenosine $A_1$ receptor.

It is demonstrated that (2-Amino-4,5,6,7-tetrahydrobenzo [b]thiophen-3-yl)(4-chlorophenyl)methanone (Compound T62) normalized hyper-excited sensory nerve functions in a model of neuropathic pain in low dosage levels.

Surprisingly, it has been found that Compound T62 is well tolerated in animals at high dosages. At these higher dosages the allosteric enhancer effect of Compound T62 can be applied to treat other pain mechanisms as well as treating neuropathic pain with higher dosages.

Compound T62

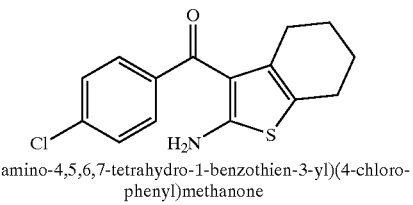

(2-amino-4,5,6,7-tetrahydro-1-benzothien-3-yl)(4-chloro-phenyl)methanone

The method of treatment comprises enteral, dermal, parenteral or subcutaneous administration of an effective amount of Compound T62, an $A_1$ allosteric enhancer, to the patient. Another object of the present invention is to provide a composition comprising an adenosine $A_1$ allosteric enhancer for the manufacture of a medicament for alleviation or normalization of a pathologically hyper-excited sensory nerve function in a conscious human subject. The invention further relates to a pharmaceutical preparation for alleviation or normalization of a pathologically hyper-excited sensory nerve function in a conscious human subject, comprising a selected allosteric enhancer for the adenosine receptor in a pharmaceutically acceptable carrier.

Accordingly, the invention provides a method using an allosteric enhancer for the $A_1$ adenosine receptor as a means to reduce or eliminate neuropathic symptoms in human subjects. An allosteric enhancer for the $A_1$ receptor is preferably administered orally in a tablet, capsule, suspension or other suitable oral dose forms. More rapid pharmacologically effect may be elicited by parenteral administration. For parental administration, it may be administered in a central vein or preferably in a peripheral vein, by a bolus injection. If desired, an allosteric enhancer can also be given intrathecally.

When given orally, a dose range of 100 mg to 1000 mg (approximately 1 to 15 mg/kg free base per dose) can be given to a patient. Doses given parentally will be in the range of 0.01 to 1 mg/kg). This treatment can be individually repeated at regular intervals. The invention is a new principle for alleviation of hypersensitivity of the sensory nerve system e.g. such as the perception of touch, temperature, vibration, pain and pressure on the skin. The invention further applies to alleviation of hyperfunction of other functions, e.g. visual function, auditory function, olfactory function, taste, balance and ganglionic transmission.

DETAILED DESCRIPTION OF THE INVENTION

Figure 1:
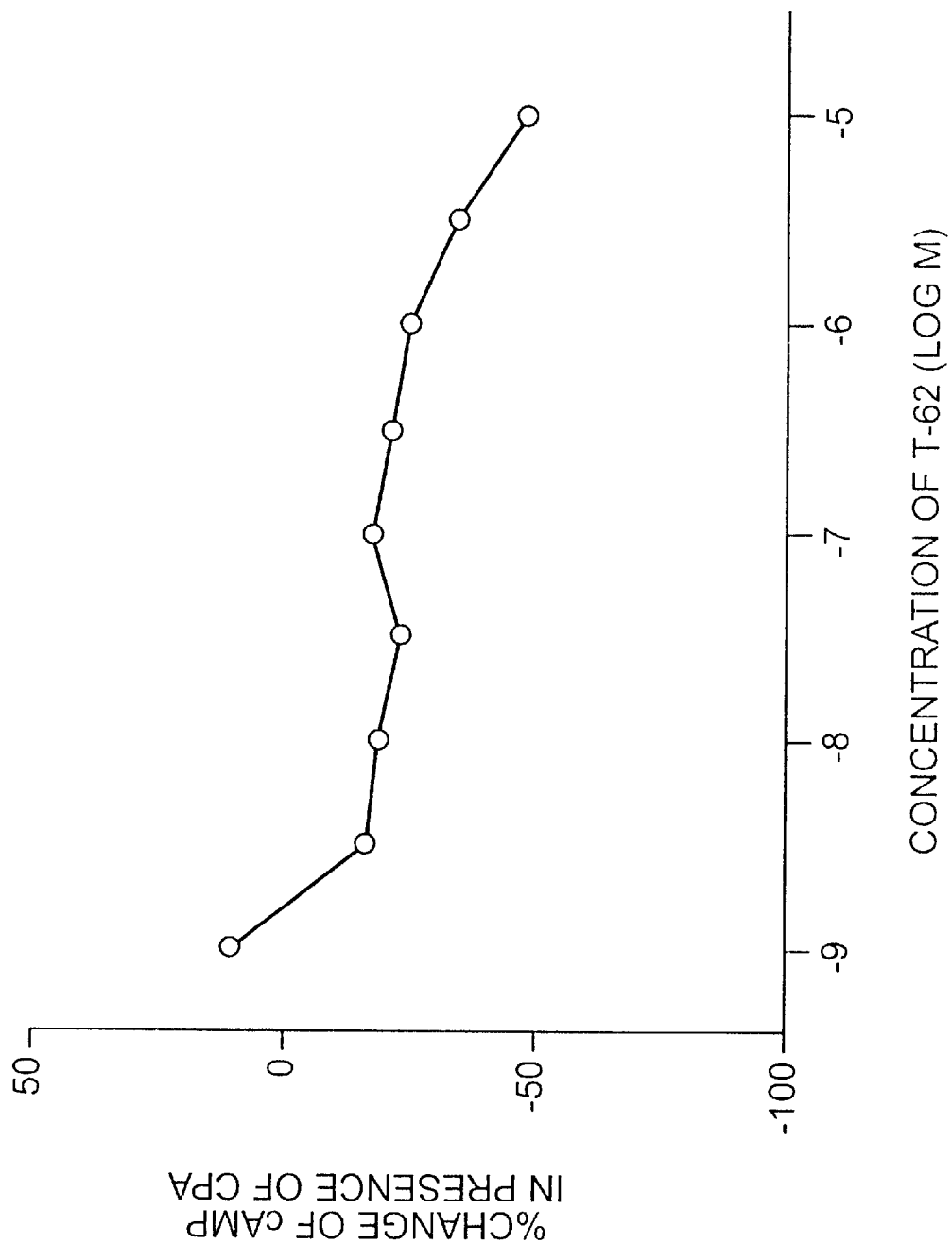
FIG. 1 is a graphic representation showing the percentage change of cAMP (adenosine 3',5'-cyclic monophosphate) in presence of CPA (N⁶-cyclopentyladenosine) in relation to Compound T62 concentration in accordance with one embodiment of the present invention.

The present invention relates to a composition and a method for the treatment of various pain states in mammal and human subjects. The treatment method comprises enteral, dermal, parenteral or subcutaneous administration of an effective amount of Compound T62, an $A_1$ allosteric enhancer, to the patient. oral administration, intravenous administration, or intrathecal administration of an allosteric enhancer at the adenosine $A_1$ receptor. It is demonstrated that (2-Amino-4,5,6,7-tetrahydrobenzo[b]thiophen-3-yl)(4-chlorophenyl)methanone (Compound T62) and pharmaceutically acceptable salts thereof are useful as the active moieties in such compositions.

Compound T62

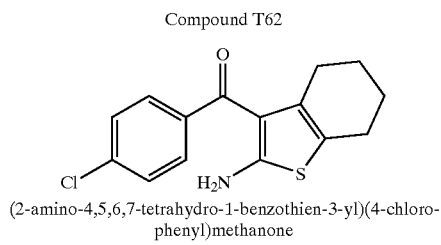

(2-amino-4,5,6,7-tetrahydro-1-benzothien-3-yl)(4-chlorophenyl)methanone

As used herein, "pharmaceutically acceptable salts" refers to pharmaceutically acceptable salts of Compound T62, which salts are derived from a variety of organic and inorganic counter ions, known in the art and include, by way of example only, sodium, potassium, calcium, magnesium, ammonium, tetra-alkylammonium, and the like; and salts of organic or inorganic acids, such as hydrochloride, hydrobromide, tartrate, mesylate, acetate, maleate, oxalate and the like that can be used as the pharmaceutically acceptable salts. Pharmaceutically acceptable salts of Compound T62 are within the scope of the present invention. As will be understood by those skilled in the art, pharmaceutically acceptable salts include, but are not limited to, salts with inorganic acids such as hydrochloride, sulfate, phosphate, hydrobromide and nitrate or salts with an organic acid such as malate, maleate, fumarate, tartrate, succinate, citrate, acetate, lactate, methanesulfonate, p-toluenesulfonate, palmoate, salicylate, and stearate. Other acids such as oxalic, while not in themselves pharmaceutically acceptable, may be useful as intermediates in obtaining the compounds of the invention and their pharmaceutical salts.

The present invention involves a method whereby the effects of endogenous adenosine are selectively enhanced at the $A_1$ adenosine receptors.

This selective enhancement will be most noticeable in organs or tissues where adenosine release is increased. We have shown that selective enhancement of the $A_1$ adenosine receptor leads to the restoration of normal sensitivity in a model of neuropathic pain at relatively low dosages. The mechanism of action for intravenous adenosine is known.

Surprisingly, it has been found that Compound T62 is well tolerated in animals at high dosages. At these higher dosages the allosteric enhancer effect of Compound T62 can be applied to treat other pain mechanisms as well as treating neuropathic pain with higher dosages.

Several reports are available explaining the mechanism of how adenosine works. Adenosine has been reported to cause pain (algogenic and hyperalgesic effects) as well as to alleviate pain (antinociceptive or analgesic effects). The mechanisms that are responsible for these opposite effects have been described in Purinergic Approaches in Experimental Therapeutics, edited by Kenneth A. Jacobson and Michael F. Jarvis, Chapter 25 entitled Purines and Nociception, by Jana Sawynok, Wiley-Liss, Inc. 1997. reviewed (14).

Briefly, activation of adenosine $A_2$ receptors in sensory nerve fibers leads to a potentiation of the nociceptive signal in several rodent pain models. This is due to a direct activation of the sensory nerve terminals as well as the release of endogenous mediators of pain such as histamine, 5-HT, substance P and other cytokines. In these animal models, adenosine and adenosine $A_1$ agonists alleviate pain by a central mechanism. Specifically, the analgesic effect of adenosine involves the $A_1$ adenosine receptors in the dorsal horn of the spinal cord. This region is where the sensory nerve fibers enter the spinal cord. The pain signals are processed in this area and then transmitted to the brain where the nociceptive signals are interpreted as pain. It is hypothesized that adenosine $A_1$ receptors suppress the nociceptive signal at the afferent nerve terminals, interneurons and the projection neurons in the dorsal spinal cord. In addition to the spinal mechanism of analgesia, administration of adenosine or $A_1$ agonists directly into the brain also produces analgesia. Therefore, supraspinal mechanisms may also contribute to the analgesia produced by adenosine and an allosteric enhancer.

The new treatment, in accordance with one embodiment of the present invention, using the $A_1$ allosteric enhancer allows an oral medication that can be given daily. Additionally, the present invention is applicable to other pharmaceutical methods for the delivery of the compound to a target area including topical applications.

One major side effect of adenosine for neuropathic pain is in the delivery. Present pharmaceutical applications of adenosine do not include oral administration and are limited to being administered by IV injection, intrathecal injection or dermal application. The advantage of the present invention is that the composition (including Compound T62) is delivered as an IV injection, intrathecal injection or by oral administration. Further, adenosine can only be delivered within a limited dose range by IV injection. For example, reference number 2 explained that at dose-rate above 70 microgram per kilogram per minute ($\mu$g/kg/min.), symptoms similar to angina pain are experienced. The lowest documented dose for efficacy for adenosine is 35 $\mu$g/kg/min. As can be seen, the therapeutic window of adenosine given intravenously only appears to have a two fold window for efficacy.

Adenosine cannot be given as a bolus injection to reduce pain. Bolus adenosine has the potential to cause heart block, which is not a desired outcome. Therefore, the reduced side effect of the present invention when compared to adenosine, include the following: a greater window of therapeutic doses without causing angina pain, avoid the need for intravenous injection, and a patient is able to administer the drug through oral doses.

Additionally, topical applications are allowed based on the effectiveness of Compound T62 as a modulator and not as an antagonist over a broader dosage range. This is particularly true since Compound T62 is effective as a modulator over the higher doses and does not behave as an antagonist at those doses. Topical application include using a formulation including Compound T62 for wound healing.

Even though there are many potential therapeutic benefits for an allosteric enhancer over an agonist for the $A_1$ adenosine receptor (10), the most potent enhancer generally known is still PD 81,723 (5, 8) first described in 1990. One explanation for the lack of progress in this field is that the enhancing action of the benzoylthiophenes is difficult to quantify. In addition, the effect of enhancers appears to be dependant on the type of test performed. In the demonstration of the applicability of the present invention, we demonstrated the following:

1. Binding studies in test tubes are not predictive of functional enhancement in cells or isolated tissues.
2. Functional studies conducted in whole cells revealed that the $A_1$ allosteric modulator of the present invention is a potent enhancer.
3. The $A_1$ allosteric modulator or enhancer or the present invention alleviates neuropathic pain in a dose dependant, time dependant manner in a rodent model of neuropathic pain.
4. The $A_1$ allosteric enhancer of the present invention is also active when given via the intrathecal route and intraperitoneal route.
5. The $A_1$ allosteric enhancer of the present invention is effective over a wider dosage range, particularly at higher concentrations, to allow application in oral or topical pharmaceutical compositions.
6. Compound T62 is a safe chemical that can be administered to animals in large quantity.
7. Compound T62 is effective in alleviating inflammatory pain.
8. Compound T62 is effective in alleviating persistent chemical pain.
9. Due to the excellent safety margin of Compound T62, and its actions on spinal and supraspinal regions that are essential for pain perception, Compound T62 is an effective treatment for all pain states. Examples of these pain states are acute pain, chronic pain, cancer pain arthropathy pain, AIDS pain, visceral pain, neuropathic pain and diabetic neuropathy.

In the work of Bruns et al. (5, 8), enhancement at the $A_1$ adenosine receptor was determined by the following methods: (a) radioligand binding at the $A_1$ receptor in rat forebrain membranes; and (b) cyclic AMP accumulation in FRTL-5 thyroid cells of the rat. Van der Klein et al. (6) also employed binding at the rat $A_1$ receptor as the method for detecting enhancement for a series of benzoylthiophenes. In both studies, (2-Amino-4,5,6,7-tetrahydrobenzo[b]thiophen-3-yl)(4-chlorophenyl)methanone (Compound T62) was described (compound 30 in (5) and compound 12N in (6)) as an enhancer with $ED_{50}$ values of 15.3 and 6.8 micromolar, respectively.

In both studies, Compound T62 was reported to be an antagonist with affinity values in the 2 to 10 micromolar range. Based on these results, one skilled in the art is led to the conclusion that Compound T62 is not a potent enhancer. From the known literature, Compound T62 is also not a useful lead because of the small separation between enhancer effects and antagonism at the $A_1$ receptor. Indeed, the best compound that has come out of these investigations is PD 81,723 (5, 6, 8, 10).

There is evidence in the literature that binding studies are not internally consistent and they also do not necessarily predict functional enhancement in vitro. For example, PD 78,416 retards the dissociation of $[^3H]CHA$ binding in rat brain (8). However, enhancement of $[^3H]CHA$ binding was not observed in rat brain in competition studies. In functional studies conducted in the isolated guinea pig left atrium and isolated ileum, PD 78,416 enhanced the effect of the agonist $N^6$-cyclopentyladenosine (CPA) in the left atrium. However, the same compound failed to enhance the effect of CPA in the isolated ileum (11). Taken together, these data point to the difficulties in predicting functional enhancement at the $A_1$ adenosine receptor.

We used the cloned human $A_1$ adenosine receptor as a tool for assaying functional enhancement produced by benzoylthiophenes (12). By this method, we have identified that Compound T62 is a potent enhancer at the cloned human $A_1$ adenosine receptor. Importantly, this compound does not antagonize the $A_1$ receptor even at a 10 micromolar concentration.

The following experiments show the effect of Compound T62 on cyclic AMP production in CHO cells expressing the $A_1$ adenosine receptor. Chinese hamster ovary cells expressing human recombinant $A_1$ adenosine receptors (CHO: huA1 cells) at a density of approximately 8000 fmol/mg protein were prepared as previously described (12) and aliquots of these cells at low passage numbers were frozen and stored in liquid nitrogen.

Cells were removed from liquid nitrogen storage when needed, and grown in Ham's F-12 culture medium with 10% fetal bovine serum and 0.5 mg/ml of antibiotic G-418. Aliquots of cells were placed into 12-well cultured plates with culture medium, serum, and antibiotic for 48–72 hours, by which time the cells had grown to a confluent monolayer.

To begin an experiment, growth medium was removed from the culture plates and cells were washed once with Hanks' buffered saline solution. The wash solution was then removed and replaced with fresh Hanks' solution containing forskolin (1 $\mu$M), rolipram (20 $\mu$M), CPA (0.05 or 1 nM), adenosine deaminase (2 U/mL), and the allosteric enhancer to be tested. After 6 min of incubation at 36° C. in the presence of drugs, the incubation solution was removed and hydrochloric (final concentration, 50 mM) was added to terminate drug action.

The content of cAMP in acidified extracts of cells was determined by radioimmunoassay as previously described (12). The compounds listed in reference 7 (U.S. Pat. No. 5,939,432) relating to allosteric enhancers, were tested using this method. None of these agents showed the high potency and the benefits seen with Compound T62, the compound of the present invention.

Because the magnitude of the effects of allosteric enhancers on cells changed with time and batch of cells, the actions of each test compound to enhance the effect of CPA (and thus reduce cAMP content of CHO cells) were normalized to the response of cells to 10 $\mu$M PD 81,723. FIG. 1 shows enhancement of the CPA induced inhibition of cyclic AMP production by Compound T62. Enhancement by Compound T62 began at 10 nM. There was no antagonism of this effect even at 10 μM of Compound T62. This study shows Compound T62 to be a more potent enhancer than PD 81,723. Also, because Compound T62 does not antagonize the $A_1$ adenosine receptor in vitro, it has a better therapeutic potential compared to PD 81,723 and other enhancers that have been reported (5, 6, 7).

The effects of the compound of the present invention on a rodent model of neuropathic pain were demonstrated as discussed below. Following Animal Care and Use Committee approval, mechanical hypersensitivity was generated in male Sprague-Dawley rats as described in the following paper. (Kim, S. H. and Chung, J. M., An experimental model for peripheral neuropathy produced by segmental spinal nerve ligation in the rat, Pain, 50 (1992) 355–363. Briefly, under general anesthesia with inhalational halothane, the left L5 and L6 spinal nerves were identified through a small laminotomy and tightly ligated. Approximately one week later, an intrathecal catheter was placed under general anesthesia by insertion under direct vision of a polyethylene catheter through a small slit in the dura at the cisterna magnum and advanced 8.5 cm such that the catheter tip resided in the lower lumbar intrathecal space. Animals were studied approximately one week later.

Ligation of the lumbar spinal nerves results in a primarily unilateral increase in the sensitivity to light touch on the operated side. Sensitivity was assessed via application of calibrated von Frey filaments. The withdrawal threshold was determined using an up down method as described in Chaplan, S. R., Bach, F. W., Pogrel, J. W., Chung, J. M., and Yaksh, T. L., Quantitative assessment of tactile allodynia in the rat paw, J. Neurosci. Methods, 53 (1994) 55–63.

In general, withdrawal threshold is 35 g or greater in animals prior to surgery, which is markedly reduced to <4 g within one week of spinal nerve ligation, and this hypersensitivity is stable for several weeks thereafter. Von Frey filaments are scientific apparatus designed to apply a predetermined pressure to a surface. These filaments are flexible bristles with a flat tip. The applied pressure is determined by the diameter of the filament.

In these studies, the animals are placed on top of a wired cage. The goal of these studies is to determine the pressure at which the animal perceives the pressure applied as painful and lifts its foot. The scientist determines the discomfort pressure threshold by pressing the tip of von Frey filaments, one filament at a time, to the bottom of the foot through the wired cage floor. When a slight pressure is applied to the underside of the foot, the animal feels the sensation but it will not lift its foot because this sensation is not painful, or uncomfortable.

In a normal animal, the threshold for discomfort is approximately 35 g pressure. In an animal whose foot is rendered more sensitive to pressure, the withdrawal threshold is less than 4 g. That is, a pressure that is not perceived as pain in the unaltered, control foot will be perceived as a painful stimulus in the surgically altered foot.

This increase in the pain response is described as hypersensitivity. Considerable research has utilized this model, which mimics several factors present in patients with chronic, neuropathic pain, including reduced sensitivity to opioids but response to alpha2-adrenergic agonists and atypical analgesics including gabapentin. Adenosine is being continually released in the spinal cord in this model, as evidenced by reduction in hypersensitivity after intrathecal injection of inhibitors of adenosine reuptake or metabolism. We tested the adenosine receptor modulator, Compound T62 to determine if it would have activity in this model and would potentiate the effects of intrathecal adenosine itself.

Mechanical withdrawal threshold was determined before and at intervals after intrathecal injection of Compound T62, 1–5 μg. Larger doses resulted in obvious motor blockade. In the study, the investigator was blinded to the dose administered. Compound T62 was dissolved in cyclodextrin, which had no effect on withdrawal threshold when administered alone. In separate experiments, animals received intrathecal adenosine, 5–30 μg, and the effect of adenosine was compared to that of Compound T62.

Animals were randomized to receive a single intrathecal injection of the allosteric adenosine receptor modulator of the present invention (referred to as Compound T62), in doses of 1, 3, or 5 μg. For comparison purposes, adenosine itself was administered in doses of 5, 10, or 30 μg. Doses of Compound T62 and adenosine were determined in pilot experiments to encompass the therapeutically effective range. Animals received 6 injections, each separated by a minimum of 4 days to prevent development of tolerance. The withdrawal threshold to mechanical stimulation with von Frey filaments was determined before and at intervals of 3 hours following intrathecal injection, then again at 20 hours following injection. A dose response was determined using the time of peak effect (2 hr for each compound) and the ED50 determined by linear regression.

In order to determine the type of interaction between intrathecal adenosine and Compound T62, an isobolographic approach was used. In this design, adenosine and T62 were combined in the ratio of their ED50s and this combination administered in different doses in a constant ratio (adenosine:Compound T62 of 7:1.8 μg, 14:3.5 μg, or 24:6 μg). The ED50 for the mixture (total of each component combined) was determined by linear regression, an isobologram constructed, and the observed ED50 was compared to the theoretical ED50 by a t-test as previously described in Tallarida, R. J., Statistical analysis of drug combinations for synergism, Pain, 49 (1992) 93–97. In order to determine the site of action of Compound T62, two experiments were performed. First, the effect of intraperitoneal injection of Compound T62, 15 mg/kg, was tested, and was noted to be effective to reduce hypersensitivity. The effect of systemic Compound T62 was then tested following intrathecal injection of the $A_1$ receptor preferring antagonist, 8-cyclopentyl-1,3-dipropylxanthine (DPCPX), 9 μg. This dose has been previously demonstrated to block the effect of adenosine to reduce hypersensitivity in rats following spinal nerve ligation. See Gomes, J. A., Li, X. H., Pan, H. L., and Eisenach, J. C., Intrathecal adenosine interacts with a spinal noradrenergic system to produce antinociception in nerve-injured rats, Anesthesiology, 91 (1999) 1072–1079.

Adenosine $A_1$ agonists produce behavioral sedation and motor blockade when administered in high doses as described in Sosnowski, M., Stevens, C. W., and Yaksh, T. L., Assessment of the role of $A_1/A_2$ adenosine receptors mediating the purine antinociception, motor and autonomic function in the rat spinal cord, J. Pharmacol. Exp. Ther., 250 (1989) 915–922. To screen for these effects, animals receiving drug treatment were observed for changes in normal exploratory behavior when placed on an open surface and were observed for signs of abnormal ambulation.

Drugs employed were adenosine (Adenocard, Fujisawa, Deerfield, Ill), DPCPX (RBI, Natick, Mass.) and Compound T62 (Medco Research, Inc, Cary, N.C. ). Compound T62 was dissolved in 45% 2-hydroxypropyl-ω-cyclodextrin (RBI, Natick, Mass. ). Drugs were administered intrathecal in a 5 μl volume followed by 10 μl of saline to flush the catheter.

Data are presented as median±25th and 75th percentile (for raw withdrawal thresholds) or by mean±SE. Linear regression was used to calculate the ED50 for each drug alone and for the fixed ratio combination. The ED50 was determined for each animal, rather than a probit analysis of the entire data set. The effect of each agent alone and the combination on withdrawal threshold over time was tested by Kruskal-Wallis analysis. P<0.05 was considered significant.

Figure 2:
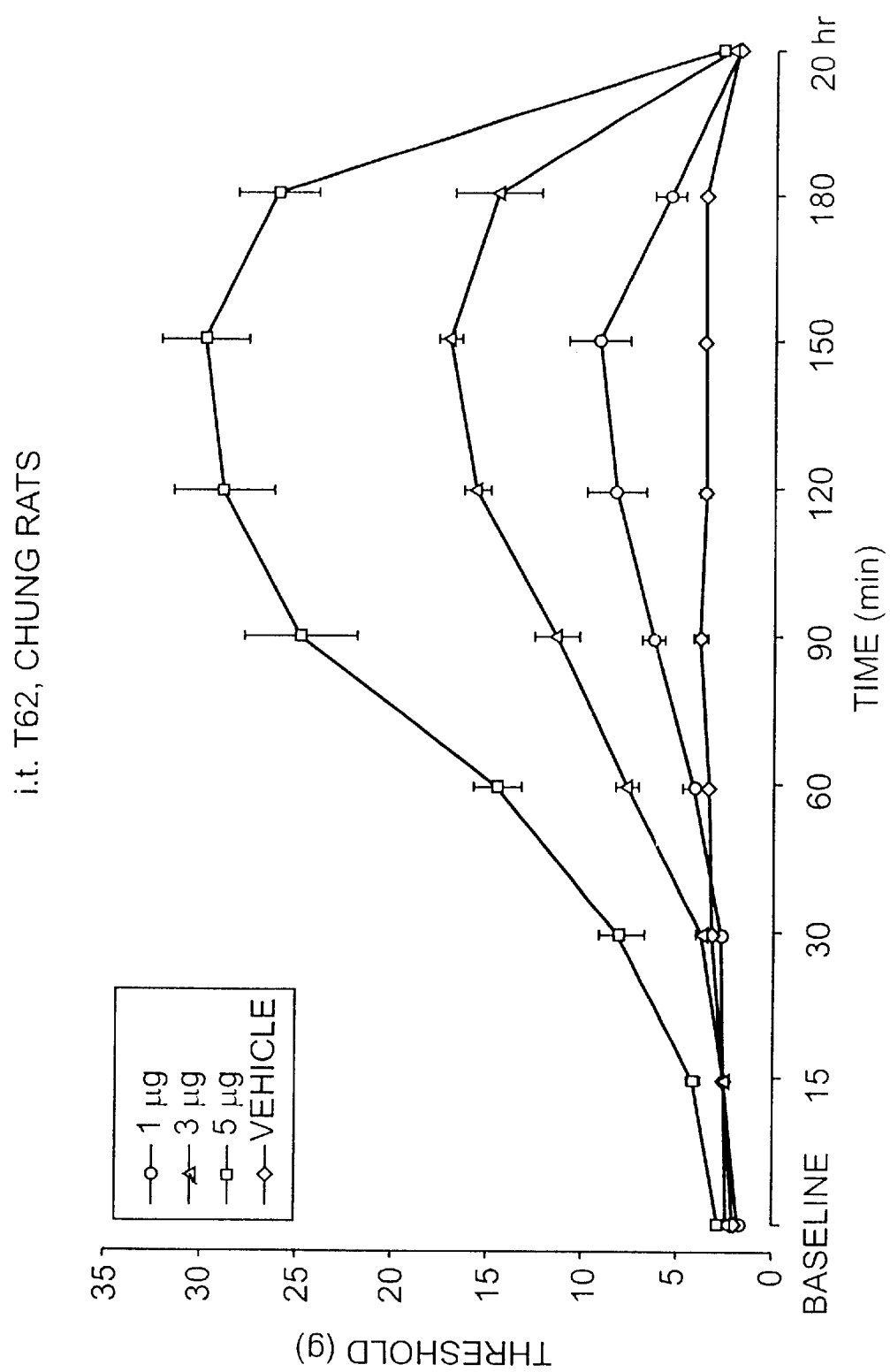
FIG. 2 is a graph showing pain threshold values versus time and Compound T62 concentration in accordance with an embodiment of the present invention.
Figure 3:
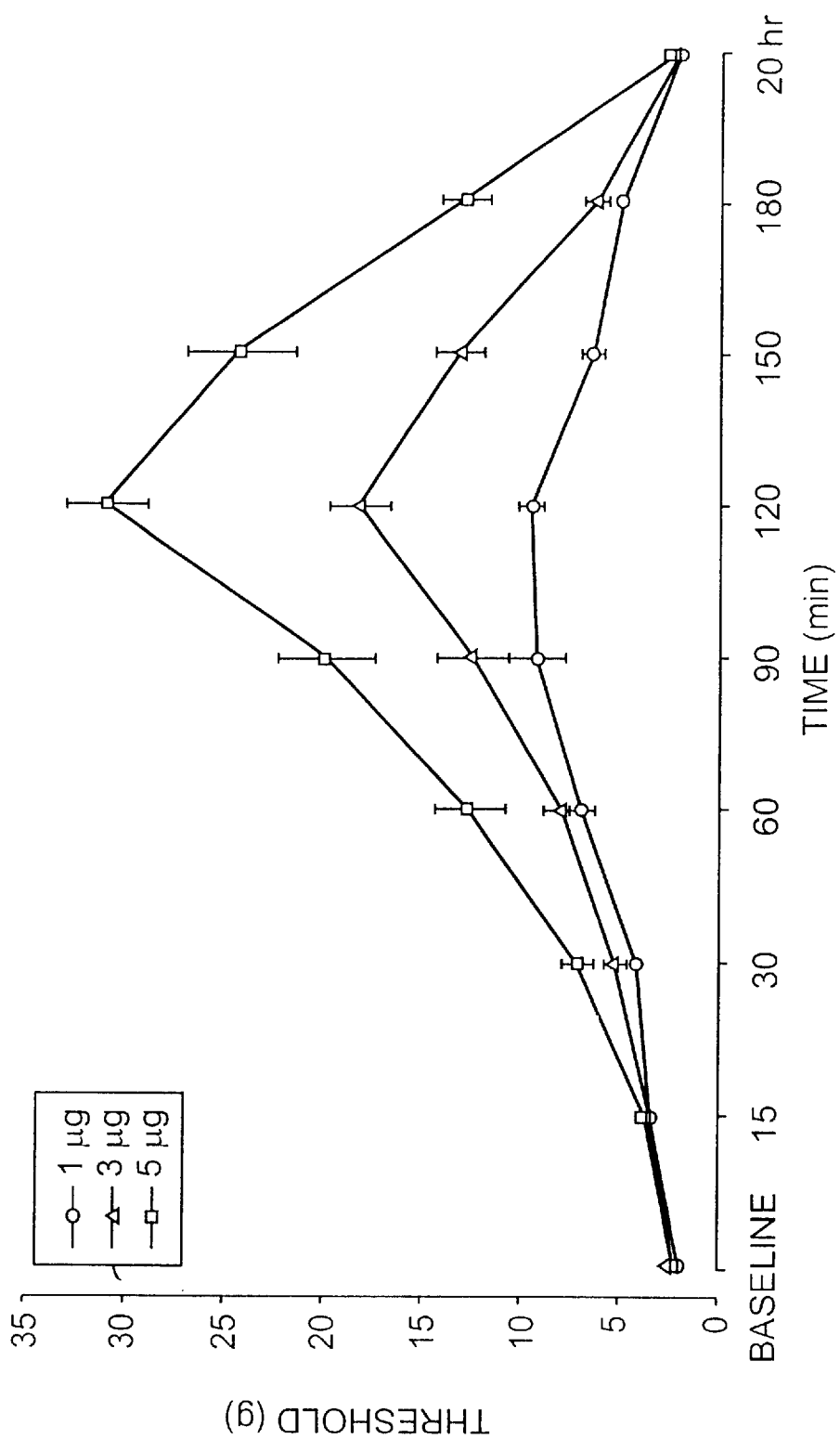
FIG. 3 is a graph illustrating pain threshold variations versus time and adenosine concentrations.
Figure 4:
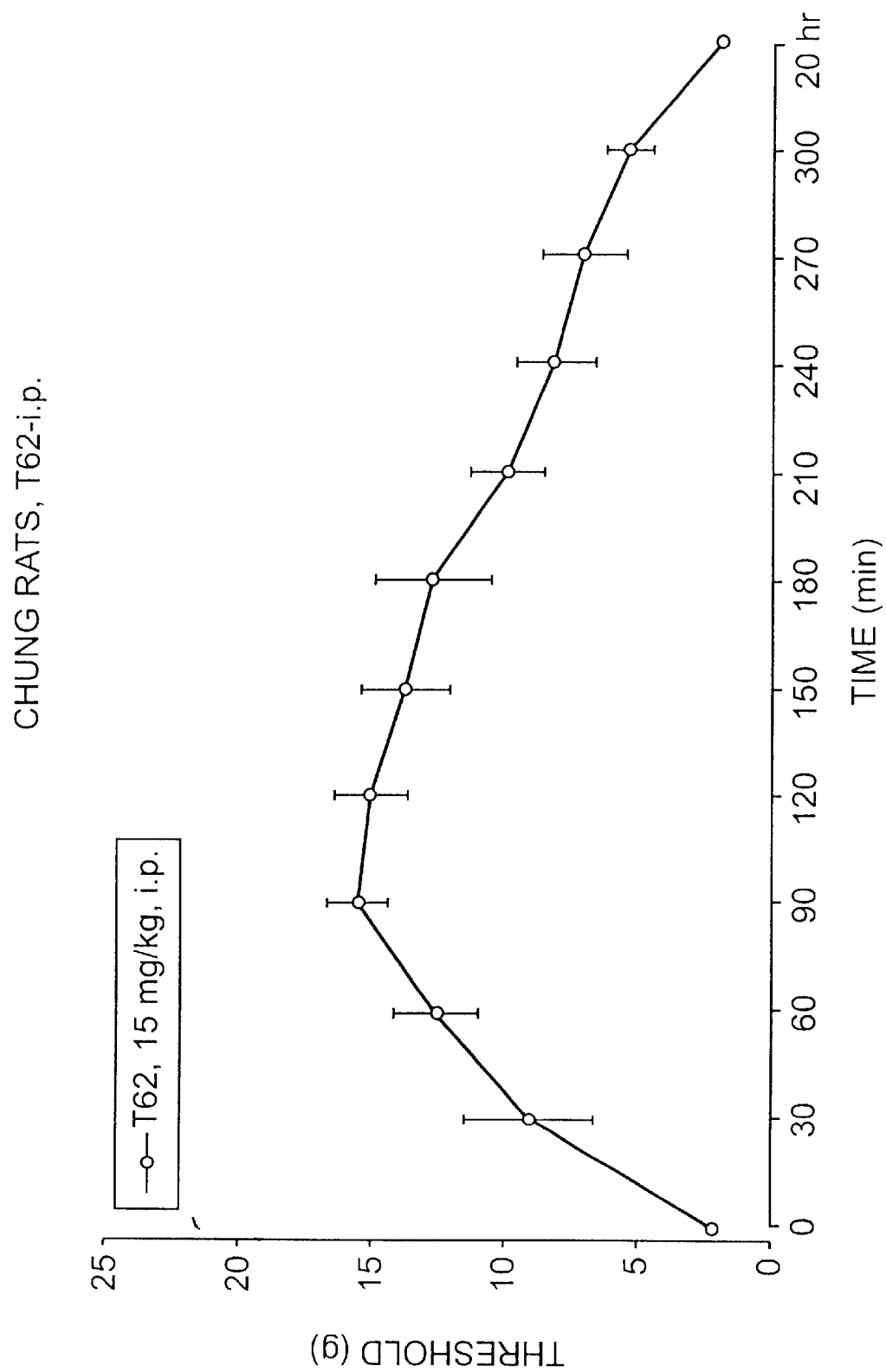
FIG. 4 is a graph illustration of pain threshold values versus time for Compound T62 in accordance with an embodiment of the present invention.
Figure 5:
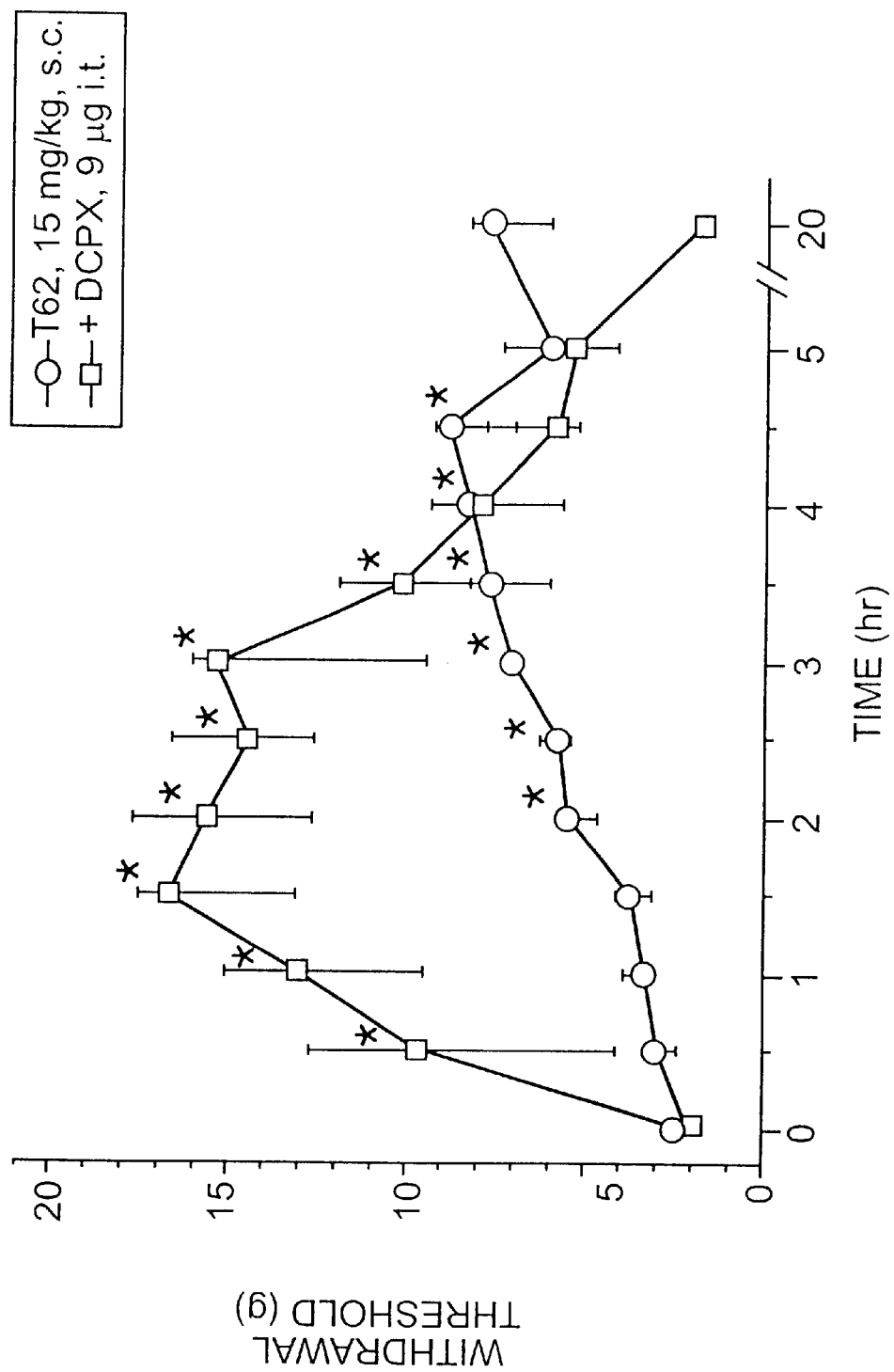
FIG. 5 is a graphical illustration of pain threshold values versus time for Compound T62 in accordance with an embodiment of the present invention.
Figure 6:
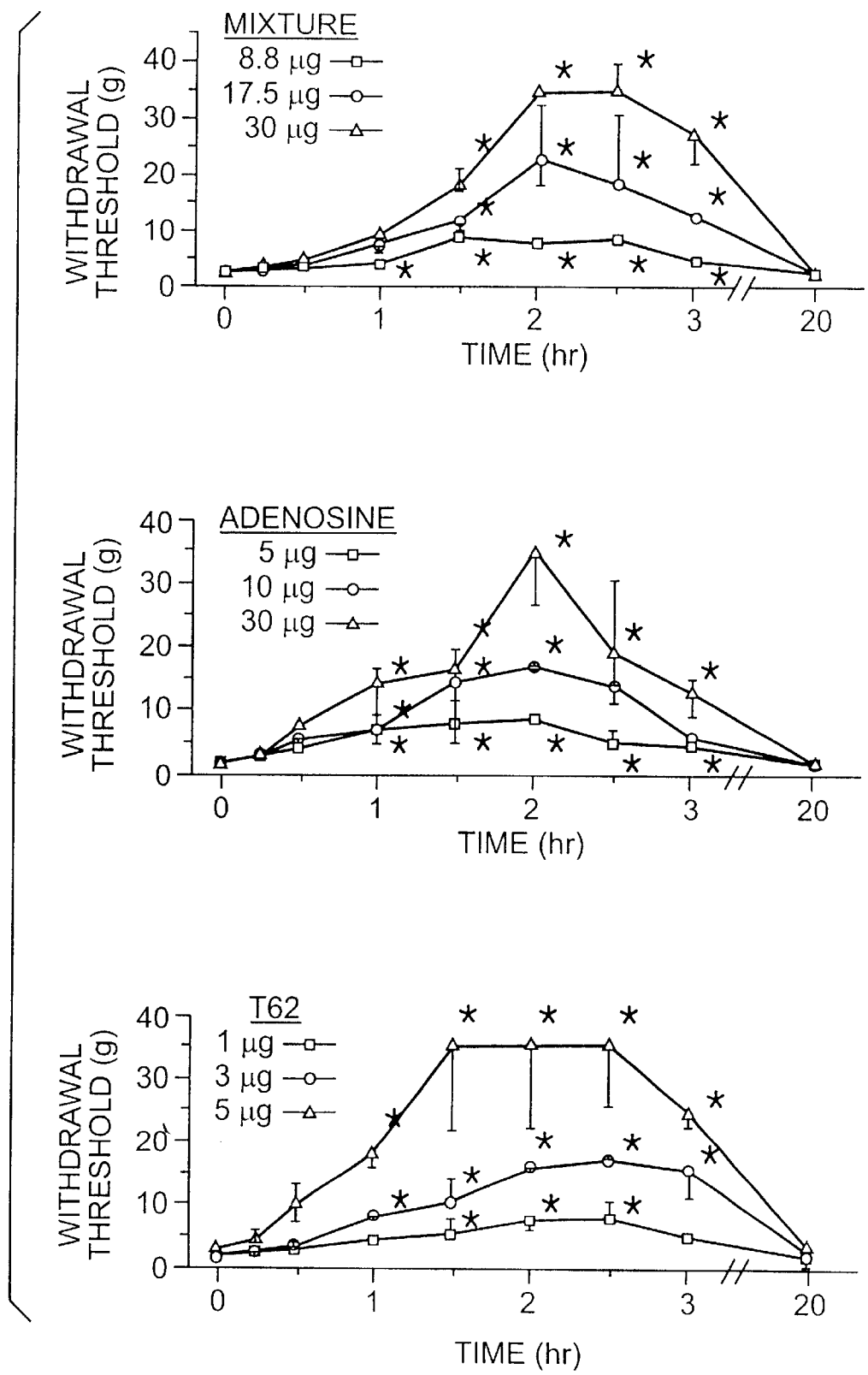
FIG. 6 includes several graphs showing the pain withdrawal threshold values for Compound T62, adenosine, and mixtures thereof versus time illustrating various embodiments of the present invention.

Results are summarized in FIGS. 2, 3, 4, which depict raw data of withdrawal threshold over time as median±25$^{th}$ and 75$^{th}$ percentiles. FIG. 2 shows intrathecal injection of Compound T62 produced dose- and time-dependent increases in withdrawal threshold, returning sensitivity to normal at the 5 µg. The effect of Compound T62 lasted over 4 hours. FIG. 3 shows a similar experiment where intrathecal adenosine produced a dose- and time-dependent increase in withdrawal threshold, returning sensitivity to normal at the 30 µg dose. FIG. 4 shows the effect of Compound T62 following intraperitoneal injection (IP) at a dose of 15 mg/kg.

The effect of Compound T62 following IP injections lasted at least 4 hours. Since Compound T62 is active after IP injection, an oral formulation containing a dose range around 15 mg/kg is useful in man for treating hyper-excited nerve activities, including neuropathic pain. In addition, the effect of Compound T62 following intraperitoneal injection is blocked by intrathecal administration of the A1 receptor antagonist DPCPX (5 µg). These results confirmed that Compound T62 is producing its effect via actions at the $A_1$ adenosine receptor in the spinal cord. The "star" points in the figures indicate that the values are significantly different from control values. That is to say that the response is considered analgesic.

As indicated above, Compound T62 is an effective treatment for neuropathic pain at a dose of 15 mg/kg by intraperitoneal (i.p.) injection. In addition, the safety of T62 was evaluated at 64, 128, 256, 512 and 1024 mg/kg (Table 1).

TABLE 1

PRIMARY OBSERVATION (IRWIN) TEST IN THE MOUSE
(3 MICE PER GROUP)
DOSE (mg/kg) i.p.

| 64 | 128 | 256 | 512 | 1024 |
|---|---|---|---|---|
| No change | No change | ↑ Fear (3/3) 15' → 30' ↑ Reactivity to touch (3/3) 15' → 30' Hyperthermia + at 180' | ↑ Fear (3/3) 15' → 30' ↑ Reactivity to touch (3/3) 15' → 30' | Tremor (3/3) → 30' Sedation + (3/3) at 30' Abnormal gait (tip-toe) (3/3) 30' → 60' ↑ Fear (3/3) 15' → 30' ↑ Reactivity to touch (3/3) 15' → 60' ↓ Muscle tone (3/3) 15' → 120' Hyperthermia + 180' → 360' |

(X/N) indicates the number of mice showing the symptoms
+ = slight.
Observations were performed up to 15 and at 30, 60, 120, 180, 360 minutes and 24 hours after administration. The symptoms which did not necessitate handling were also observed up to 15 minutes immediately following administration. Hyperthermia was evaluated by comparison of the mean scores obtained in treated and control animals.

Even at the higher dosages, no overt signs of toxicity were observed. Compound T-62, administered intraperitoneally, induced no change from control at 64 and 128 mg/kg. It induced signs of hypersensitivity to external stimulation (increased fear and increased reactivity to touch) and slight hyperthermia from 256 mg/kg, with tremor and tip-toe gait at 1024 mg/kg, the highest dose tested. At this highest dose, Compound T62 also induced slight sedation and decreased muscle tone. As is therefore disclosed, Compound T62 is a very safe chemical entity relative to its projected clinical doses.

EXAMPLE

Inflammatory Pain

Compound T62 was tested for its efficacy in treating inflammatory pain by use of the carrageenan paw model. Carrageenan is a water-extractable polysaccharide obtained from seaweeds. Injection of lambda carrageenan (a hydrocolloid that does not form a gel) into the plantar foot, or the knee joint, results in a localized inflammation that leads to decreased weight bearing, guarding of the affected limb, and hyperalgesia. Carrageenan-induced hyperalgesia is believed to occur as a consequence of sensitization of primary afferent nociceptors and neuron plasticity intrinsic to the spinal cord.

Animals were prepared with chronic lumbar intrathecal catheters. Baseline measurement of hindpaw withdrawal latency to thermal stimulation were obtained on a Hargreaves device. Animals received a single intrathecal (IT) injection of Compound T-62 ranging from 0.5 to 40 µg. Withdrawal thresholds were measured on a Hargreaves device every 30 minutes for three hours.

Compound T-62 had no significant effect on withdrawal thresholds in normal rats. In rats that have received an intraplantar injection of 2 mg of carrageenan in their right hind paw, even 1 µg of T-62 was sufficient to completely reverse hypersensitivity of the inflamed foot to pre-carrageenan levels (n=4). These data are consistent with studies in rats and human receiving IT adenosine itself, and infer that Compound T62 is particularly effective in correcting setting of hypersensitivity back to the normal range. Therefore, Compound T62 is an effective treatment for inflammatory pain.

EXAMPLE

Persistent Chemical Pain/General Analgesic Activity

Testing for use of Compound T62 in treatment of persistent chemical pain was performed following the phenylbenzoquinone (PBQ) writhing tests. This method detects general analgesic activity. Mice were injected with phenylbenzoquinone (PBQ) (1.25 mg/kg i.p.). This treatment induced a recognizable writhing response in control animals. The number of writhes was counted for 10 minutes beginning 5 minutes after injection of PBQ. 8 mice were studied for each treatment group and the test was performed blind. Results of this study are shown in Table 2.

TABLE 2

EFFECTS OF Compound T62 IN THE PHENYLBENZOQUINONE-INDUCED MOUSE WRITHING TEST (8 MICE PER GROUP)

| T-62 (mg/kg) | NUMBER OF WRITHES (5 to 15 min after phenylbenzoquinone) | | |
|---|---|---|---|
| | mean ± s.e.m. | p value | percent change from control |
| i.p. −30 minutes | | | |
| Vehicle | 16.9 ± 2.9 | — | — |
| 128 | 13.9 ± 3.4 NS | 0.515 | −18% |
| 512 | 5.9 ± 2.2 ** | 0.009 | −65% |
| i.p. −1 hour | | | |
| Vehicle | 25.9 ± 5.2 | — | — |
| 128 | 10.9 ± 2.6 * | 0.021 | −58% |
| 512 | 6.4 ± 1.0 ** | 0.002 | −75% |
| i.p. −2 hours | | | |
| Vehicle | 27.6 ± 6.5 | — | — |
| 128 | 17.3 ± 2.0 NS | 0.151 | −38% |
| 512 | 3.5 ± 1.8 ** | 0.003 | −87% |
| i.p. −4 hours | | | |
| Vehicle | 20.5 ± 4.8 | — | — |
| 128 | 13.1 ± 3.5 NS | 0.232 | −36% |
| 512 | 4.8 ± 1.5 ** | 0.007 | −77% |
| i.p. −8 hours | | | |
| Vehicle | 13.8 ± 3.1 | — | — |
| 128 | 15.3 ± 4.1 NS | 0.775 | +11% |
| 512 | 6.0 ± 1.9 NS | 0.052 | −56% |

NS = Not Significant;
* = p < 0.05;
** = p < 0.01

These data demonstrate that Compound T62 is effective in this model of chemically induced pain. Interestingly, the doses required for efficacy appeared to be higher than that required for neuropathic pain following intraperitoneal administration (15 mg/kg in rats versus 128 mg/kg in mice, table 2). Compound T62 is safe even at doses up to 1012 mg/kg, intraperitoneally. Due to the excellent safety profile that has been demonstrated for Compound T62 (see above), it is possible to deliver Compound T62 in a very wide dose range (15 mg/kg i.p. to 1,204 mg/kg intraperitoneally) for the relief of different pain states.

The data disclosed shows that Compound T62 is a very effective treatment for inflammatory pain. This compound is also effective for chemically induced, persistent pain. The data have demonstrated that a higher dose of Compound T62 is required for chemically induced, persistent pain. Since Compound T62 can be safely administered to a subject at very high doses (up to 1024 mg/kg, intraperitoneally), Compound T62 is useful for treating all pain states. It is particularly potent in pain states that involved hypersensitivity of the nociceptive pathway such as neuropathic pain and inflammatory pain. At higher doses, Compound T62 is effective in acute pain states such as that induced by chemical irritation, gastrointestinal disturbance, migraine and all forms of headache.

Depending on the pain states and the dose required for treatment, Compound T62 can be delivered by the oral route, intravenous route, intramuscular route, subcutaneous route, intrathecal route topical, dermal route, intranasal route, inhalation system, suppository delivery system or other forms of suitable drug delivery systems.

While the present invention includes the co-administration of adenosine with Compound T62, this co-administration is not essential. It is preferred to administer Compound T62 alone for economic and drug interaction reasons. Adenosine is released from the hyperexcited nerves. The formulation of the present invention (Compound T62) enhances the effect of endogenous adenosine released from the hyper-excited nerves. Because adenosine is not released everywhere all at once, that is why this treatment method provides site specific, event-specific beneficial effects. For example, for the patients suffering from neuropathic pain, the enhancer amplifies the analgesic effect of endogenous adenosine and produces pain relief. This patient will not suffer symptoms of a heart attack because the release of adenosine is not being stimulated in the heart. Topical applications of the present invention also allow the localized usage of the $A_1$ allosteric modulator.

One advantage of the present invention is the ability to use the compound over a wide dosage range with various modes of administration, including oral administration. One of the options includes the administration of Compound T62 as an intravenous bolus injection. For the bolus administration, the preferred dose range is from about 0.1 milligrams (mg) to about 15 mg per kg. The most preferred dose range is from about 1 to about 5 mg per kilogram.

For administration in the form of an oral dose, the preferred range is from 1 mg to 1000 mg. The most preferred range is from 10 to 500 mg range.

In one embodiment of the present invention, a formulation comprising Compound T62 is administered as a tablet, capsule, caplet, coated tablet, capsule containing various smaller sizes coated particles, and the like. The pill is given as an oral medication once or twice daily for treating symptoms of neuropathic pain. Two per day are an option, one for daytime use and one for nighttime use. Since there is the potential of an enhancer to cause sedation at a high dose, the higher doses are recommended for night use. For example, a dose of from 100 to 500 mg dose of Compound T62 in tablet form is recommended for daytime use while a dose from 600 to 1000 mg is recommended as a nighttime dose.

Although specific embodiments of the present invention have been described in detail, it should be understood that the present invention may be embodied in many other specific forms without departing from the scope of the invention as recited in the claims.

The following references are indicative of the level of skill in the art and provide background for the present invention. The disclosures of all these references are hereby incorporated by reference in their entirety.

1. Sollevi, A. Method of treating hyperexcited sensory nerve function. U.S. Pat. No. 5,691,318, 1997.
2. Sollevi, A. Adenosine for pain control. Acta Anaesthesiol. Scand. Suppl. 110: 135–136, 1997.
3. Belfrage M., Segerdahl M., Arner S., Sollevi A. The safety and efficacy of intrathecal adenosine in patients with chronic neuropathic pain. Anesth. Analg. 89:136–142, 1999.
4. Ralevic V. and Burnstock, G. Receptors for Purines and Pyrimidines. Pharmacol. Rev. 50: 413–492, 1998.
5. Bruns, R. F., Fergus, J. H., Coughenour, L. L., Courtland, G. g., Pugsley, T. A., Dodd, J. H., Tinney, F. J. Structure-activity relationships for enhancement of adenosine A1 receptor binding by 2-amino-3-benzoylthiophenes. Mol. Pharm. 38: 950–958, 1990.
6. van der Klein, P. A., Kourounakis, A. P. and ljzerman, A. P. Allosteric modulation of the adenosine A(1) receptor. Synthesis and biological evaluation of novel 2-amino-3- benzoylthiophenes as allosteric enhancers of agonist binding. J Med Chem 42: 3629–3635, 1999.
7. Baraldi, P. G. Thiophenes useful for modulating the adenosine receptor. U.S. Pat. No. 5,939,432, 1999.
8. Bruns, R. F. and Fergus, J. H. Allosteric enhancement of adenosine A1 receptor binding and function by 2-amino-3-benzoylthiophenes. Mol. Pharmacol. 38: 939–949, 1990.
9. Poulson, S. A. and Quinn, R. J. Adenosine receptors: new opportunities for future drugs. Bioorg. Med. Chem. 6:619–641, 1998.
10. Linden, J. Allosteric enhancement of adenosine receptors. In Purinegic Approaches in Experimental Therapeutics, edited by K. A. Jacobson and M. F. Jarvis, 1997 Wiley-Liss, pp85–97.
11. Leung, E. Walsh, L. K. M., Flippin, L. A. Kim, E. J., Lazar, DE. A., Seran, C. S., Wong, E. H. F. and Eglen, R. M. Enhancement of adenosine A1 receptor functions by benzoylthiophenes in guinea pig tissues in vitro. Naunyn-Schmiedeberg's Arch. Pharmacol. 352: 206–212, 1995.
12. Shryoick, J. C., Ozeck, M. J. and Belardinelli, L. Inverse agonists and neutral antagonists of recombinant human A1 adenosine receptors stably expressed in chinese hamster ovary cells. Mol. Pharmacol. 53: 886–893, 1993.
13. Kim, S. H. and Chung, J. M. An experimental model for periphereal neuropathy produced by segmental spinal nerve ligation in the rat. Pain, 50: 355–363, 1992.
14. Sawynok, J. Purines and Nociception. In Purinergic Approaches in Experimental Therapeutics, Edited by K. A. Jacobson and M. F. Jarvis. 1997 Wiley-Liss, pp495–513.
15. Yaksh, T. L. Spinal systems and pain processing: development of novel analgesic drugs with mechanistically defined models. Trends in Pharmacological Sciences 20, 329 337, 1999.
16. Jarvis, M. F., Yu, H., Kohlhass, K., Alexander, K, Lee, C.-H., Jiang, M., Bhagwat, S. S., Williams, M. and Kowaluk, E. A. ABT-702 (4-Amino-5-(3-bromophenyl)-7-(6-morpholino-pyridin-3-yl)pyrido[2,3-d]pyrimidine), a novel orally effective adenosine kinase inhibitor with analgesic and anti-inflammatory properties: I. In vitro characterization and acute antinociceptive effects in the mouse. J. Pharm. Exp. Ther. 295, 1156–1164, 2000.
17. Kowaluk, E. A., Mikusa, J., Wismer, C. T., Zhu, C. Z., Schweitzer, E., Lynch, J. L., Lee, C.-H., Jiang, M, Bhagwat, S. S., Gomtsyan, A., McKie, J., Cox, B. F., Polakowski, J., Reinhart, G., Williams, M. and Jarvis, M. F. ABT-702 (4-Amino-5-(3-bromophenyl)-7-(6-morpholino-pyridin-3-yl)pyrido[2,3-d]pyrimidine), a novel orally effective adenosine kinase inhibitor with analgesic and anti-inflammatory properties. II. In vivo characterization in the rat. J. Pharm. Exp. Ther. 295, 1165–1174, 2000.
18. McGaraughty, S., Chu, K. L., Wismer, C. T., Mikusa. J., Zhu, C. Z., Cowart, M., Kowaluk, E. A. and Jarvis, M. F. Effects of A-134974, a novel adenosine kinase inhibitor, on carrageenan-induced inflammatory hyperalgesia and locomotor activity in rats: evaluation of the sites of action. J. Pharm. Exp. Ther. 296, 501–509, 2001.

What is claimed is:

1. A method of treating hyper-excited sensory nerve functions, comprising administering to a conscious human patient in need of treatment thereof a pharmaceutical composition comprising an effective amount of (2-Amino-4,5,6,7-tetrahydrobenzo[b]thiophen-3-yl)(4-chlorophenyl)methanone or a pharmaceutically acceptable salt thereof in a dose of from 45 µg/kg to 1024 µg/kg.

2. The method of claim 1 wherein the administering to the patient includes administration via topical, oral, subcutaneous, intramuscular, intrathecal, and intravenous applications.

3. The method of claim 1 wherein the administration is by intraperitoneal injection.

4. The method of claim 1 wherein the disorder to be treated is selected from the group consisting of hyperesthesia, dysesthesia, allodynia, hyperalgesia, tinnitus, ganglionic dysfunction and combinations thereof.

5. A method of treating hyper-excited sensory nerve functions, comprising administering to a conscious human patient in need of treatment thereof a pharmaceutical composition comprising an effective amount of (2-Amino-4,5,6,7-tetrahydrobenzo[b]thiophen-3-yl)(4-chlorophenyl)methanone or a pharmaceutically acceptable salt thereof in a dose of from 45 µg/kg to 1024 µg/kg and adenosine.

6. The method of claim 4 wherein the administering to the patient includes administration via topical, oral, subcutaneous, intramuscular, intrathecal, and intravenous applications.

7. The method of claim 4 wherein the administration is by intraperitoneal injection.

8. The method of claim 4 wherein the disorder to be treated is selected from the group consisting of hyperesthesia, dysesthesia, allodynia, hyperalgesia, tinnitus, ganglionic dysfunction and combinations thereof.

9. A pharmaceutical preparation for oral administration to a human for the reduction of neuropathic pain and inflammatory pain comprising (2-Amino-4,5,6,7-tetrahydrobenzo[b]thiophen-3-yl)(4-chlorophenyl)methanone or a pharmaceutically acceptable salt thereof in dosage levels of from 45 µg/kg to 1024 µg/kg.

10. A pharmaceutical preparation for oral administration to a human for the reduction of neuropathic pain and inflammatory pain comprising (2-Amino-4,5,6,7-tetrahydrobenzo[b]thiophen-3-yl)(4-chlorophenyl)methanone or a pharmaceutically acceptable salt thereof in dosage levels of from 45 µg/kg to 1024 µg/kg and further comprising adenosine.

11. A method of treating hyper-excited sensory nerve functions, comprising administering to a patient in need of treatment thereof an oral pharmaceutical composition comprising an effective amount of (2-Amino-4,5,6,7-tetrahydrobenzo[b]thiophen-3-yl)(4-chlorophenyl)methanone or a pharmaceutically acceptable salt thereof in dosage levels of from 45 µg/kg to 1024 µg/kg.

12. The method of claim 11 wherein the administering to the patient of the oral pharmaceutical composition comprises giving the patient at least two doses per twenty four hours, a first dose for daytime use having a lower concentration of 2-Amino-4,5,6,7-tetrahydrobenzo[b]thiophen-3-yl)(4-chlorophenyl)methanone or a pharmaceutically acceptable salt thereof, and a second dose for nighttime use having a higher concentration of 2-Amino-4,5,6,7-tetrahydrobenzo[b]thiophen-3-yl)(4-chlorophenyl)methanone or a pharmaceutically acceptable salt thereof.

13. The method of claim 11 wherein the first dose for daytime use comprises from 1000 to 5000 milligrams of 2-Amino-4,5,6,7-tetrahydrobenzo[b]thiophen-3-yl)(4-chlorophenyl)methanone or a pharmaceutically acceptable salt thereof, and the second dose for nighttime use comprises from 5000 to 10,000 milligrams of (2-Amino-4,5,6,7-tetrahydrobenzo[b]thiophen-3-yl)(4-chlorophenyl)methanone or a pharmaceutically acceptable salt thereof.

14. A method of treating inflammatory pain, comprising administering to a mammal in need of treatment thereof a pharmaceutical composition comprising an effective amount of 2-Amino-4,5,6,7-tetrahydrobenzo[b]thiophen-3-yl)(4-chlorophenyl)methanone or a pharmaceutically acceptable salt thereof.

15. The method of claim 14 wherein the composition is administered in a dose of from 45 µg/kg to 1024 µg/kg.

16. The method of claim 14 wherein the first dose for daytime use comprises from 1000 to 5000 milligrams of 2-Amino-4,5,6,7-tetrahydrobenzo[b]thiophen-3-yl)(4-chlorophenyl)methanone or a pharmaceutically acceptable salt thereof, and the second dose for nighttime use comprises from 5000 to 10,000 milligrams of (2-Amino-4,5,6,7-tetrahydrobenzo[b]thiophen-3-yl)(4-chlorophenyl)methanone or a pharmaceutically acceptable salt thereof.

17. A method of treating persistent chemical pain, comprising administering to a mammal in need of treatment thereof a pharmaceutical composition comprising an effective amount of (2-Amino-4,5,6,7-tetrahydrobenzo[b]thiophen-3-yl)(4-chlorophenyl)methanone or a pharmaceutically acceptable salt thereof.

18. The method of claim 17 wherein the composition is administered in a dose of from 5 µg/kg to 1024 µg/kg.

19. The method of claim 17 wherein the first dose for daytime use comprises from 1000 to 5000 milligrams of 2-Amino-4,5,6,7-tetrahydrobenzo[b]thiophen-3-yl)(4-chlorophenyl)methanone or a pharmaceutically acceptable salt thereof, and the second dose for nighttime use comprises from 5000 to 10,000 milligrams of (2-Amino-4,5,6,7-tetrahydrobenzo[b]thiophen-3-yl)(4-chlorophenyl)methanone or a pharmaceutically acceptable salt thereof.

20. A method of treating pain states, comprising administering to a mammal in need of treatment thereof a pharmaceutical composition comprising an effective amount of (2-Amino-4,5,6,7-tetrahydrobenzo[b]thiophen-3-yl)(4-chlorophenyl)methanone or a pharmaceutically acceptable salt thereof.

21. The method of claim 20 wherein the pain states are selected from the group of pain states consisting of acute pain, chronic pain, cancer pain, arthropathy pain, AIDS pain, visceral pain and diabetic neuropathy.

22. The method of claim wherein the composition is administered in a dose of from 5 µg/kg to 1024 µg/kg.

23. The method of claim wherein the first dose for daytime use comprises from 1000 to 5000 milligrams of 2-Amino4,5,6,7-tetrahydrobenzo[b]thiophen-3-yl)(4-chlorophenyl)methanone or a pharmaceutically acceptable salt thereof, and the second dose for nighttime use comprises from 5000 to 10,000 milligrams of (2-Amino-4,5,6,7-tetrahydrobenzo[b]thiophen-3-yl)(4-chlorophenyl)methanone or a pharmaceutically acceptable salt thereof.

24. A pharmaceutical preparation for oral administration to a human for the reduction of pain states comprising (2-Amino-4,5,6,7-tetrahydrobenzo[b]thiophen-3-yl)(4-chlorophenyl)methanone or a pharmaceutically acceptable salt thereof.

25. The pharmaceutical preparation of claim 24 wherein the preparation comprises a dose of from 5 µg/kg to 1024 µg/kg of (2-Amino-4,5,6,7-tetrahydrobenzo[b]thiophen-3-yl)(4-chlorophenyl)methanone or a pharmaceutically acceptable salt thereof.

26. The method of claim 24 wherein the pain states are selected from the group of pain states consisting of acute pain, chronic pain, cancer pain, arthropathy pain, AIDS pain, visceral pain and diabetic neuropathy.

* * * * *